(12) United States Patent
Hörnig

(10) Patent No.: US 8,366,764 B2
(45) Date of Patent: Feb. 5, 2013

(54) STENT FOR POSITIONING IN A BODY CONDUIT OR METHOD FOR PRODUCING THIS STENT

(75) Inventor: Mathias Hörnig, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 624 days.

(21) Appl. No.: 12/231,666

(22) Filed: Nov. 7, 2008

(65) Prior Publication Data

US 2009/0062902 A1 Mar. 5, 2009

Related U.S. Application Data

(62) Division of application No. 11/442,887, filed on May 30, 2006, now abandoned.

(30) Foreign Application Priority Data

May 30, 2005 (DE) .......................... 10 2005 024 625

(51) Int. Cl.
*A61F 2/06* (2006.01)
(52) U.S. Cl. ...................................................... 623/1.21
(58) Field of Classification Search .................... 623/1.21
See application file for complete search history.

(56) References Cited

U.S. PATENT DOCUMENTS

| | | | | |
|---|---|---|---|---|
| 5,092,841 A * | 3/1992 | Spears | ...................... | 604/103.01 |
| 5,344,444 A | 9/1994 | Glastra | | |
| 5,575,815 A * | 11/1996 | Slepian et al. | ................... | 600/36 |
| 5,725,568 A * | 3/1998 | Hastings | ........................ | 623/1.21 |
| 5,749,922 A * | 5/1998 | Slepian et al. | ................ | 29/469.5 |
| 5,785,679 A * | 7/1998 | Abolfathi et al. | .............. | 604/509 |
| 5,899,917 A * | 5/1999 | Edwards et al. | ............... | 606/195 |
| 6,176,871 B1 * | 1/2001 | Pathak et al. | .................. | 623/1.21 |
| 6,482,179 B1 * | 11/2002 | Chu et al. | ................... | 604/164.09 |
| 6,569,190 B2 * | 5/2003 | Whalen et al. | .................. | 623/1.1 |
| 6,689,148 B2 * | 2/2004 | Sawhney et al. | .............. | 606/193 |
| 7,083,643 B2 * | 8/2006 | Whalen et al. | ................ | 623/1.42 |
| 7,156,872 B2 * | 1/2007 | Strecker | ........................ | 623/1.24 |
| 2003/0134032 A1 * | 7/2003 | Chaouk et al. | ............... | 427/2.24 |
| 2004/0093069 A1 * | 5/2004 | Priewe et al. | ................. | 623/1.15 |
| 2004/0093074 A1 | 5/2004 | Hildebrand et al. | | |

(Continued)

FOREIGN PATENT DOCUMENTS

DE 692 02 308 T2 1/1993
DE 201 19 322 U1 3/2002

(Continued)

OTHER PUBLICATIONS

"Quality . . . Measured in Outcomes"; IOMED GmbH; [retrieved from Internet on] Jun. 13, 2006; [retrieved from Internet at] http://www.iomed.com, p. 1.

(Continued)

*Primary Examiner* — David Isabella
*Assistant Examiner* — Leslie Coburn

(57) ABSTRACT

By a contrast means contained in an inventive stent which has a greater permeability for x-radiation features than the body tissue surrounding the stent in a relevant body conduit, this stent can be clearly detected in its position on an x-ray image of the relevant body conduit while at the same time exhibiting good biological compatibility; a gas, especially one contained in cavities of the stent is provided as a contrast means. The inventive production method for this stent with the aid of a catheter embodied specially for the purpose enables the production of the stent from a malleable polymer mass in the relevant body conduit so that the stent is adapted especially precisely to the shape of the relevant body conduit.

11 Claims, 3 Drawing Sheets

U.S. PATENT DOCUMENTS

| | | | |
|---|---|---|---|
| 2004/0148014 A1* | 7/2004 | Nuutinen et al. | 623/1.15 |
| 2004/0236410 A1* | 11/2004 | Herweck et al. | 623/1.21 |
| 2005/0004584 A1* | 1/2005 | Franco et al. | 606/155 |
| 2010/0331947 A1* | 12/2010 | Shalev et al. | 623/1.11 |

FOREIGN PATENT DOCUMENTS

| | | | |
|---|---|---|---|
| EP | 1 464 300 A1 | 10/2004 | |
| WO | WO 94/24962 A1 | 11/1994 | |

OTHER PUBLICATIONS

"Marker Band Swaging Equipment Uses Flexures to Guide Motion"; ThomasNet, IndustrialNews Room; Oct. 23, 2002; [retrieved from Internet on] Jun. 9, 2006; [retrieved from Internet at] http://industrialnewsroom.com/fullstory/15429, pp. 1-4.

* cited by examiner

STENT FOR POSITIONING IN A BODY CONDUIT OR METHOD FOR PRODUCING THIS STENT

CROSS REFERENCE TO RELATED APPLICATIONS

This is a divisional application of U.S. patent application Ser. No. 11/442,887, filed May 30, 2006, now abandoned which claims priority of German application No. 10 2005 024 625.7 filed May 30, 2005. Both applications are incorporated by reference herein in their entirety.

FIELD OF THE INVENTION

The invention relates to a stent for positioning in a body conduit or to a method for producing this stent, with the stent containing a contrast means for x-radiation.

BACKGROUND OF THE INVENTION

A stent is a tubular implant which provides radial outwards support for the wall of a body conduit, e.g. a blood vessel, bile duct, an air conduit or an esophagus. The stent usually consists of the elastic material, e.g. a metal or metal alloy or a polymer, and frequently has a mesh or network or spiral-type structure, with stents in the form of a metal mesh being the most widely used. The stent is introduced into the relevant body conduit with the aid of a catheter and is bought into adhesive contact there with the wall of the body conduit. With blood vessels specifically stents are introduced into the wall of the vessel as endoluminal vessel prostheses for therapy of stenoses caused by arterosclerotic plaque.

A stent is known from US 2004/0148014 A1 in which markers are impermeable to x-rays are distributed, in order to make the position of the stent clearly visible on an x-ray image when it has been used in the relevant body conduit. These markers most contain substances such as heavy metals or iodine compounds which, when used in the body conduit—even with an appropriate encapsulation—present a potential danger to health.

SUMMARY OF THE INVENTION

The object of the present invention is to specify a stent which is simple to produce, which, despite being easily visible on an x-ray image, still exhibits good biological compatibility without a potential danger to health.

This object is achieved by a stent or by a method in accordance with the independent claims. Advantageous embodiments of the invention are the subject of the assigned dependent claims in each case.

Through the inventive contrast means contained in the stent, which has a greater permeability for x-radiation than body tissue surrounding the stent in the relevant body conduit, the introduction of a potentially hazardous contrast means with a lower permeability for x-radiation in the body conduit is avoided and yet easy identification of the stent introduced into the relevant body conduit on an x-ray image of the body conduit is still guaranteed.

Contrast means with a higher permeability for x-radiation than the surrounding body tissue in each case are known as negative contrast means. They are shown as dark areas on an x-ray image. On the other hand contrast means with a lower permeability for x-radiation than the surrounding body tissue it are referred to as positive contrast means. They are shown as light areas on the x-ray image. Unlike positive contrast means which, as a result of the compounds that they contain with elements with a high atomic number, are at least potentially damaging to health, negative contrast means mostly have good biological compatibility.

A negative contrast means in the form of a gas, especially in the form of carbon dioxide, enables an especially high permeability for x-radiation and thus an especially good detectability of the position of the stent in the body conduit on the X-ray image. As a rule gases exhibit a far lower atomic density than a solid or a liquid with the same substance so that gases of the low atomic density are accordingly particularly permeable for x-radiation. In addition, gases, especially carbon dioxide, are inexpensive by comparison with the usual positive contrast means.

By enclosing the gas in cavities of the stent on the one band the stability of the stent is increased and on the other hand by selecting an appropriate distribution density of the cavities or through the form of the hollow cavities the elastic properties of the stent can be adapted to the relevant purpose for which it is used or to the relevant body conduit. Tubular cavities extending in the longitudinal direction of the stent for example allow the stent to be bent easily in the longitudinal direction without this process reducing the radial stability of the stent. In addition, the stent is then also still able to be detected on the x-ray image if for example a few cavities are not gas-tight and some of the gas escapes when the stent is positioned, during its expansion or during its time in the body conduit. In addition, a stent with cavities containing the gas is simple and cheap to produce.

A stent consisting at least partly of a polymer guarantees especially good biocompatible properties and a low-cost production of the stent. The stent can for example consist entirely of the polymer or be coated with the polymer. A stent made entirely of polymer, such as silicone or rubber for example, where necessary except for the negative contrast means, is, in addition, especially elastic and can also be easily adapted to a distortion of the body conduit.

In accordance with one embodiment of invention, the polymer is embodied in the form of a polymer foam containing the cavities. A stent consisting of this polymer foam is especially simple to produce by foaming up the polymer with the gas. Polyurethane is suitable for example as the polymer and can be foamed up in a manner known per-se with little effort. The still liquid polymer can be foamed up in the production of the stent both by introducing the gas into it and by letting a gas dissolved in the polymer escape.

In accordance with a further embodiment of the invention, the polymer is embodied in the form of small polymer balls containing the cavities. These can be incorporated into the stent particularly easily, e.g. by mixing the polymer balls with a liquid material from which the stent is formed, in which case the liquid material itself can again also be a polymer.

The inventive method of production for the stent consisting at least partly of the polymer provides a simple means of producing the stent which is clearly visible on the x-ray image and yet is still biologically compatible. The stent is simultaneously positioned in the body conduit using a catheter positioned in the body conduit. The stent has a filling area at least partly enclosing this catheter which can be filled with a polymer mass to be hardened into the stent. In addition, the stent is precisely adapted to the form of the relevant body conduit by its being formed in the body conduit so that the stent is secured against slippage in the body conduit and damage to the body conduit by the stent is avoided.

In accordance with an embodiment of the invention there is advantageous provision for filling the filling area positioned at the position intended for the stent with a polymer mass temporally accommodated in an inner chamber of the catheter. In this way, especially for simple introduction of the catheter into the body conduit, it is possible to fill the filling area with the plastic mass only when the position intended for the stent is reached.

BRIEF DESCRIPTION OF THE DRAWINGS

The invention, as well as further advantageous embodiments of the invention in accordance with features of the dependent claims, are explained in greater detail below with reference to schematic diagrams of exemplary embodiments in the drawing, without this restricting the invention to this exemplary embodiment in any way. The Figures show:

DETAILED DESCRIPTION OF THE INVENTION

Figure 1:
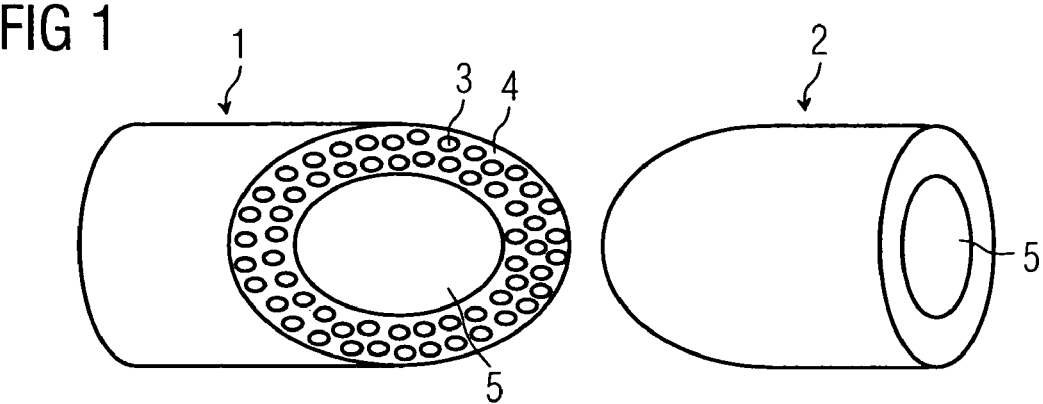
FIG. 1 in a perspective view, a stent divided into two parts made of a polymer, with a contrast means in the form of a gas enclosed in cavities.

FIG. 1 shows in a perspective view, a stent made of a polymer which is shown in a cross section at right angles to the longitudinal direction of the stent, divided into a first part 1 and a second part 2, in order to make the cavities 3 surrounded by the polymer and filled with a gas visible in a sectional surface 4 of the first part 1.

There is provision to feed a catheter through an opening 5 passing through the stent 1, 2 and to place the stent 1, 2 on the catheter in such a way that the stent encloses an expandable balloon section of the catheter in the form of a tube. Subsequently the stent 1, 2 is introduced with the aid of the catheter into a body conduit and is adapted there to the internal diameter of the body conduit by an expansion of the balloon section. Finally the catheter is removed while the stent 1, 2 remains in the body conduit and provides radial support for this.

The gas contained in the cavities, e.g. carbon dioxide, operates as a negative contrast means so that the position of the stent 1, 2 within the body conduit can be detected on an x-ray image of the body conduit. The more gas that is enclosed in the ratio by volume to the remaining stent material in the stent 1, 2 the clearer the image of the stent 1, 2 that stands out as a dark area against the image of the body tissue surrounding the stent 1, 2.

The stent, after its expansion into its expanded form, retains this form even after the catheter has been removed. The stent consists at least partly of a plastic deformable material which permanently assumes its changed shape through a radial expansion. This material can for example be embodied in the form of a number of rings distributed over the length of the stent 1, 2 and surrounding the opening 5 in each case.

Alternatively it is also possible to arrange an elastically deformable wire mesh within the stent 1, 2 which keeps the stent 1, 2 in the expanded state after its expansion.

Figure 2:
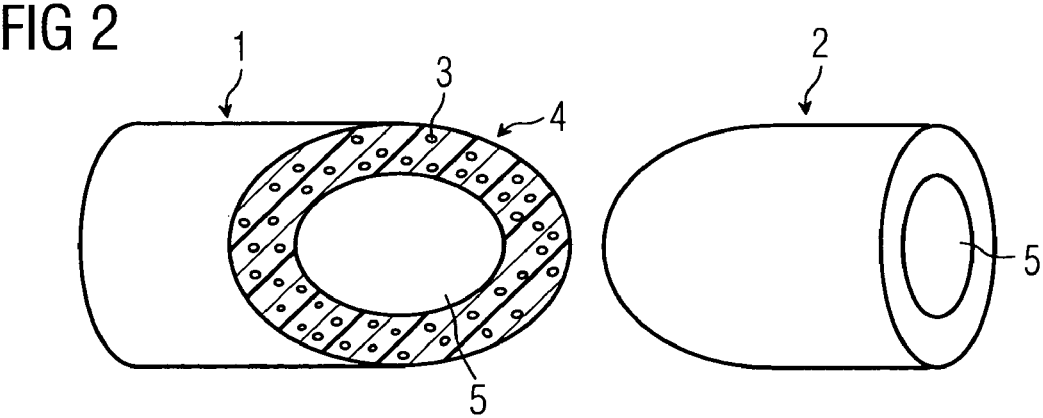
FIG. 2 a stent as shown in FIG. 1 made of a polymer foamed up with the gas.

FIG. 2 like FIG. 1, shows a stent 1, 2 made of polymer, with the polymer being embodied in the form of a polymer foam which can be seen from the cross-sectional surface 4. The negative contrast means in the form of a gas is enclosed in the cavities 3 of the polymer foam.

Figure 3:
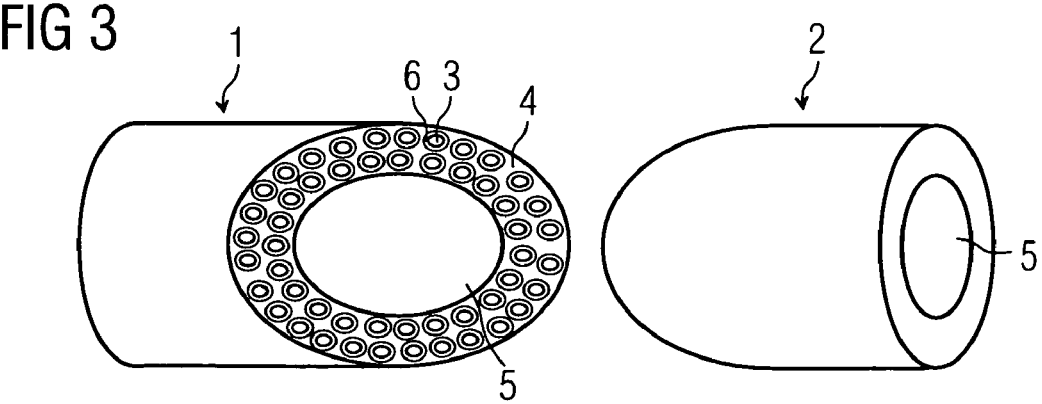
FIG. 3 a stent as shown in FIG. 1 with the small polymer balls containing the gas.

FIG. 3 like FIGS. 1 and 2, shows a stent 1, 2 made of polymer, with the polymer being embodied in the form of small polymer balls 6 which can be seen from the cross-sectional surface 4. The negative contrast means is enclosed in gaseous form in the cavities of the polymer foam. The other stent material surrounding the small polymer balls in the stent 1, 2 can be both the same polymer and also another substance, such as a second polymer for example.

Instead of a surface enclosed in a radial direction, the stent 1, 2 can also have a surface in the form of a mesh or in the form of a grid.

FIGS. 4-7 illustrate typical examples based on an exemplary embodiment for the inventive method for producing a stent 20 by means of a catheter 8 with simultaneous positioning of the stent 20 in a body conduit 7.

Figure 4:
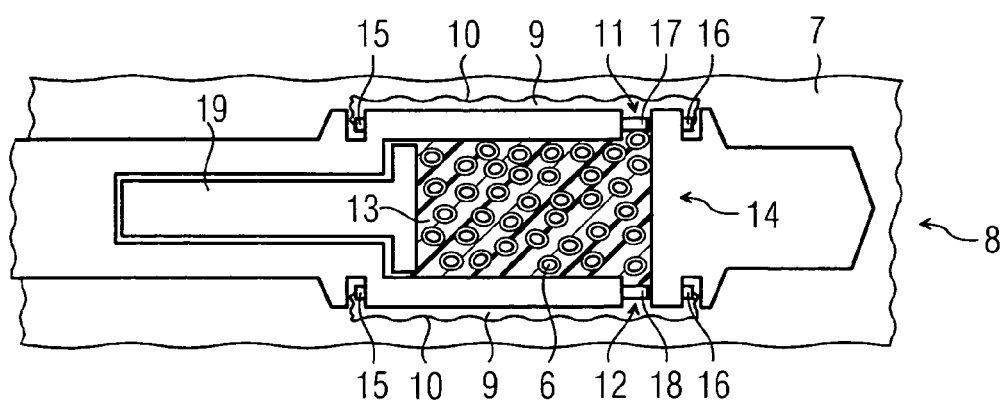
FIG. 4 in a longitudinal cross-section, a catheter introduced into the body conduit with a filling area which is enclosed by an envelope and able to be filled with a polymer mass which is held in a capsule arranged in a catheter.

FIG. 4 shows in a longitudinal cross section a catheter 8 introduced into a body conduit 7 with an essentially tubular filling area 9 surrounding the catheter 8 which is enclosed by an envelope 10 and which is connected via two filling openings 11 or 12 to an inner chamber in the form of a cylindrical capsule 14 arranged in the catheter containing a liquefied and hardenable polymer mass 13. The envelope 10 is held onto the catheter at its front and rear end by an extendable and retractable clamping ring 15 or 16 which encloses the entire circumference of the catheter 8 in each case, so that the filling area 9 is completely sealed off from the body conduit 7. The two filling openings 11 and 12 each have an opening slider 17 or 18, with which the filling openings 11 or 12 respectively are closed off. To fill the filling area 9 with the polymer mass 13 from the capsule 14, a piston 19 which can be pushed within the capsule 14 is provided. The clamping rings 15 or 16, the opening sliders 17 or 18 and also the piston 19 are remotely operated automatically or at least partly with the involvement of an operator of the catheter 8. The catheter 8 is already positioned with its filling area 9 at the position intended for the stent.

In an especially uncomplicated manner the polymer mass 13 is mixed with the negative contrast means before the filling area 9 is filled with this polymer mass 13. This removes the need for separate filling of the filling area 9 with the polymer mass 13 and with the negative contrast means 6. In this exemplary embodiment the negative contrast means in the form of the small polymer balls 6 filled with carbon-dioxide is mixed in homogeneously with the polymer mass 13 before the catheter 8 is introduced into the body conduit 7.

Depending on the contrast means used in each case it is also possible to have the filling area 9 filled with the negative contrast means before it is filled with the polymer mass 13.

When a contrast means in the form of a gas, especially in the form of carbon dioxide is used, this is distributed especially easily and cost-effectively by foaming up the polymer mass with the gas in the stent 8. The foaming-up of the gas can be undertaken both before and also after the filling of the filling area with the polymer mass 13. In the case of letting the gas escaping into the polymer, this process is expediently undertaken in the filling area 9.

Figure 5:
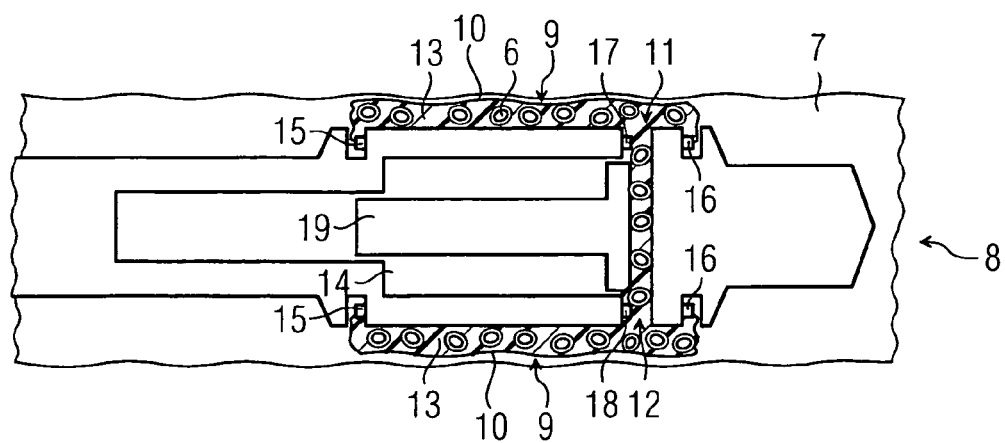
FIG. 5 the catheter shown in FIG. 4 with the filling area being filled with the polymer mass and thereby expanded towards the wall of the body conduit.

FIG. 5 shows the catheter 8 shown in FIG. 4 with the filling openings 11 and 12 opened by moving one of the opening sliders 17 or 18 and the piston 19 pushed into the capsule 14, so that the filling area is filled with the polymer mass 13 from the capsule 14. Filling the filling area with the polymer mass 13 expands the filling area so that is advantageously adapts its form and size to the body conduit 7. In this case the expansion does not create any undesired expansion forces since the liquefied polymer mass 13 can distribute itself to match the wall of the body conduit 7.

After the filling openings 11 or 12 have been closed again the polymer mass 13 is hardened to create the stent 20, depending on the polymer simply after a hardening period.

Figure 6:
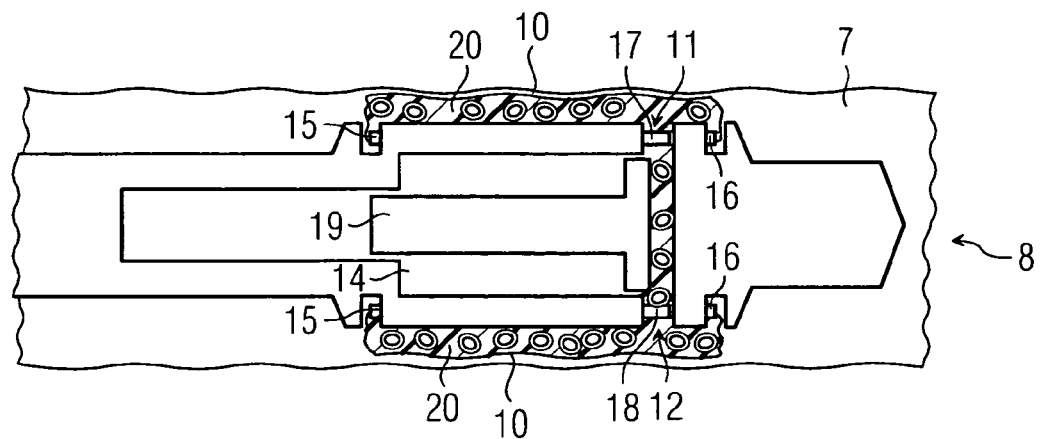
FIG. 6 the catheter shown in FIG. 4 with the filling openings from the capsule to the filling area closed and the envelope separated from the catheter.

FIG. 6 shows the catheter 8 shown in FIG. 5, with the filling openings 11 or 12 being closed again for an especially simple removal of the catheter 8 from the body conduit 7, especially before the hardening of the polymer mass 13. In FIG. 6 the polymer mass 13 is already hardened into the stent 20 and, in addition, the envelope 11 is released from a catheter 8 by retraction of the clamping rings 15 or 16. In this state it is possible to withdraw the catheter 8 from the body conduit 7 with the stent 20 simultaneously remaining in the body conduit 7.

To adapt the stent 20 in respect of its internal diameter an inflatable balloon section surrounded by the filling area (9) is additionally provided which is inflated after the positioning of the filling area 9 at the position intended for the stent 20.

Figure 7:
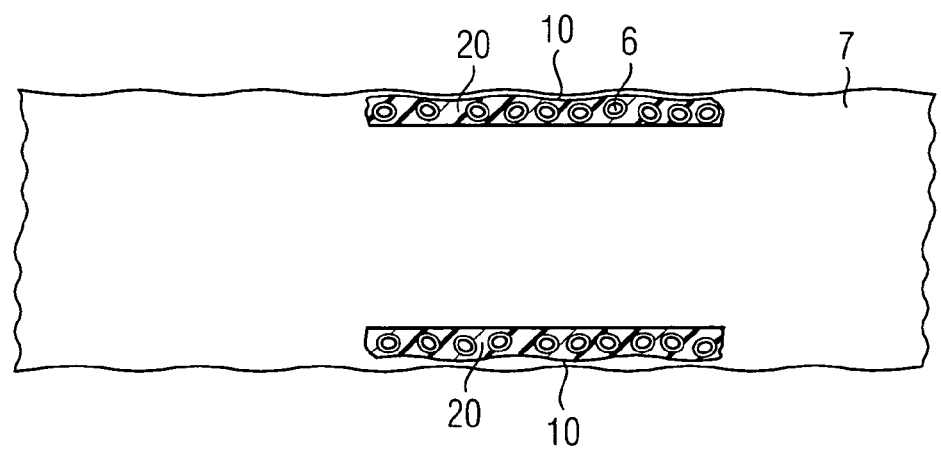
FIG. 7 the body conduit shown in FIG. 4-6 with the stent produced by the catheter.

FIG. 7 shows the body conduit 7 shown in the FIGS. 4-6 with the stent 20 produced by the catheter 8 after the removal of the catheter 8 from the body conduit 7, with the envelope released from a catheter 8 remaining with the stent 20 in the body conduit 7 as a component of the latter. By using a material which can be broken down biologically in the body conduit 7 for the envelope, the envelope 10 which is essentially only needed to produce the stent 20 is broken down after a period depending on the material used in each case.

By mixing the negative contrast means into the polymer mass 13 the stent 20 produced from this polymer mass 13 is easy to be detected on an x-ray image of the body conduit 7.

In an advantageous manner a means for liquefying or for hardening of the polymer mass 13 by a change of temperature is provided. This enables the polymer mass 13, because of its good deformability in the liquid state, to be particularly well adapted to the properties of the body conduit 7 and enables the filling area 9 to be filled especially simply. It is possible to arrange a heating element in the catheter 8 for liquefying or hardening of the polymer mass 13 by heating it up.

To enable stents of different lengths to be produced with the same catheter, further clamping rings can be provided between the clamping rings 15 or 16. The envelope 10 is accordingly held with one of its ends by clamping ring 16 and with its other end by one of the other clamping rings.

The invention can be summarized as follows: Through a contrast means contained in an inventive stent which exhibits a higher permeability for x-radiation than body tissue surrounding the stent in a relevant body conduit, this stent can be clearly detected in its position on the x-ray image of the relevant body conduit and at the same time has good biological compatibility. A gas contained in a cavities of the stent is in particular provided as the contrast means. The inventive production method for this stent with the aid of a catheter embodied especially for the purpose enables the production of the stent from a malleable polymer mass in the relevant body conduit so that the stent is adapted especially precisely to the shape of the relevant body conduit.

The invention claimed is:

1. A method for forming a stent in a body conduit of a patient, comprising:
   positioning a catheter at a position of the body conduit where the stent is intended to be placed;
   arranging a tubular filling area enclosed by an envelope surrounding and attached to a part of the catheter;
   filling the tubular filling area with a hardenable polymer mass, wherein the tubular filling area is in fluid communication with an inner chamber of the catheter which contains the polymer mass during the positioning step;
   hardening the polymer mass in the tubular filling area, such that the hardened polymer mass is enclosed by the envelope, wherein the hardened polymer mass and the envelope together form the stent; and
   removing the catheter from the body conduit with the stent remaining in the body conduit.

2. The method as claimed in claim 1, wherein a contrast medium is mixed with the polymer mass or brought into the filling area before the filling.

3. The method as claimed in claim 2, wherein the contrast medium has a higher permeability for an x-radiation than body tissues surrounding the stent which makes the stent to be easily visible in an x-ray image.

4. The method as claimed in claim 2, wherein the contrast medium is a gas and distributed by foaming up the polymer mass with the gas in the stent.

5. The method as claimed in claim 4, wherein the gas is a carbon dioxide.

6. The method as claimed in claim 1, wherein the filling area is expandable by filling with the hardenable polymer mass.

7. The method as claimed in claim 1, wherein the inner chamber is a closable capsule.

8. The method as claimed in claim 7, wherein an opening from the inner chamber to the filling area is closed off after the filling and before the removal of the catheter from the body conduit.

9. The method as claimed in claim 8, wherein the opening from the inner chamber to the filling area is closed off after the filling and before the hardening of the polymer mass.

10. The method as claimed in claim 1, wherein the polymer mass is liquefied or hardened in the filling area by a temperature change.

11. The method as claimed in claim 1, wherein a balloon section of the catheter surrounded by the filling area is inflated after positioning the catheter in the body conduit.

\* \* \* \* \*